(12) United States Patent
Zhu et al.

(10) Patent No.: US 9,989,520 B2
(45) Date of Patent: Jun. 5, 2018

(54) HUMAN HEPATOMA CELL LINE HLCZ01 AND USES THEREOF

(71) Applicant: HUNAN PROVINCIAL TUMOR HOSPITAL, Changsha, Hunan (CN)

(72) Inventors: Haizhen Zhu, Changsha (CN); Chaohui Zuo, Changsha (CN); Xiaohong Wang, Changsha (CN); Darong Yang, Changsha (CN); Nianli Liu, Changsha (CN)

(73) Assignee: HUNAN UNIVERSITY, Changsha, Hunan (CN)

( * ) Notice: Subject to any disclaimer, the term of this patent is extended or adjusted under 35 U.S.C. 154(b) by 0 days. days.

(21) Appl. No.: 14/414,886

(22) PCT Filed: May 10, 2013

(86) PCT No.: PCT/CN2013/075459
§ 371 (c)(1),
(2) Date: Jan. 14, 2015

(87) PCT Pub. No.: WO2014/117454
PCT Pub. Date: Aug. 7, 2014

(65) Prior Publication Data
US 2015/0204855 A1    Jul. 23, 2015

(30) Foreign Application Priority Data

Feb. 1, 2013  (CN) .......................... 2013 1 0041142
May 7, 2013  (CN) .......................... 2013 1 0164388

(51) Int. Cl.
*G01N 33/50*   (2006.01)
*C12Q 1/68*   (2018.01)
*G01N 33/574*   (2006.01)
*C12N 5/09*   (2010.01)
*C12N 5/071*   (2010.01)

(52) U.S. Cl.
CPC ......... *G01N 33/5067* (2013.01); *C12N 5/067* (2013.01); *C12N 5/0693* (2013.01); *C12Q 1/6886* (2013.01); *G01N 33/57438* (2013.01); *C12Q 2600/136* (2013.01); *C12Q 2600/158* (2013.01); *G01N 2333/765* (2013.01); *G01N 2333/91188* (2013.01)

(58) Field of Classification Search
CPC ...... A61K 2035/124; A61K 2039/5152; A61K 38/1709; C12N 7/00; C12N 15/907; C12N 5/0068; C12N 5/0663; C12N 5/069; C12N 2500/99; C12N 2500/90; C12N 2501/00; C12N 2503/00; C12N 2510/00
See application file for complete search history.

(56) References Cited

U.S. PATENT DOCUMENTS 4,393,133 A  * 7/1983 Knowles .............. C07K 14/005
424/227.1

FOREIGN PATENT DOCUMENTS

WO    WO 2014117454 A1  * 8/2014 ........... A61K 35/407

OTHER PUBLICATIONS

Yang D, Zuo C, Wang X, Meng X, Xue B, Liu N, Yu R, Qin Y, Gao Y, Wang Q, Hu J, Wang L, Zhou Z, Liu B, Tan D, Guan Y, Zhu H. Complete replication of hepatitis B virus and hepatitis C virus in a newly developed hepatoma cell line. Proc Natl Acad Sci U S A. Apr. 1, 2014;111(13):E1264-73. Epub Mar. 10, 2014.*

* cited by examiner

*Primary Examiner* — Rachel B Gill
(74) *Attorney, Agent, or Firm* — Raymond Y. Chan; David and Raymond Patent Firm

(57) ABSTRACT

A human hepatoma cell line is HLCZ01 cell line which has been deposited in the China Center for Type Culture Collection (CCTCC), and having Accession (deposit) No. is CCTCC NO: C201309. The human hepatoma cell line HLCZ01 is used as a cell model supporting said hepatitis viruses infection and is used to establish an animal model for supporting virus infection, wherein said human hepatoma cell line HLCZ01 is also used for preparation, screening and evaluating anti-hepatitis virus drugs, anti-tumor drugs, and used for manufacturing artificial liver.

11 Claims, 15 Drawing Sheets

Amount of RNA of the hepatitis B virus

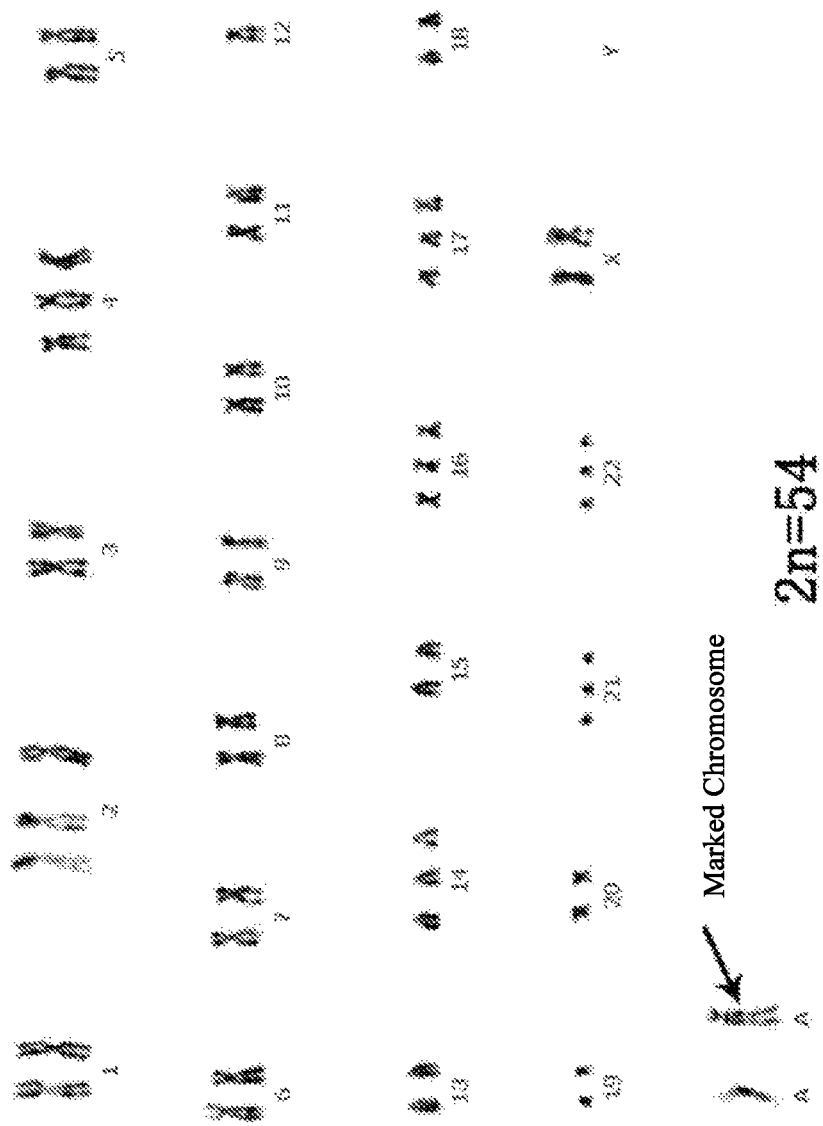

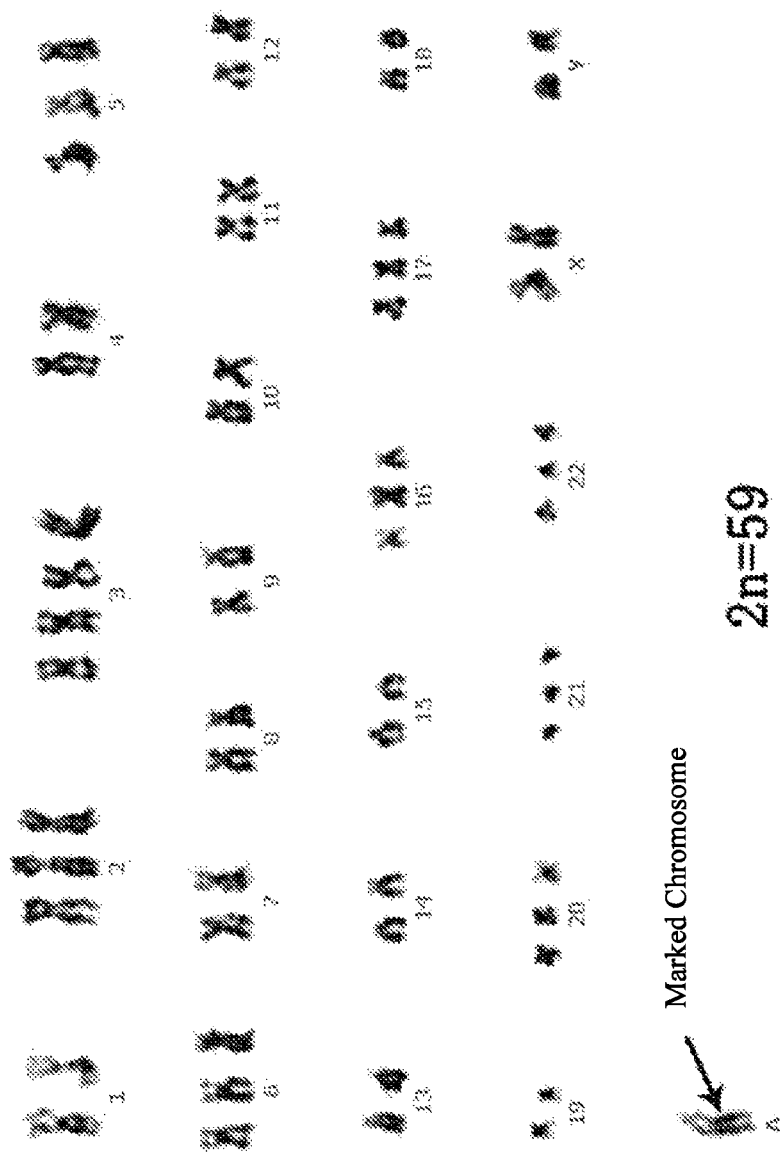

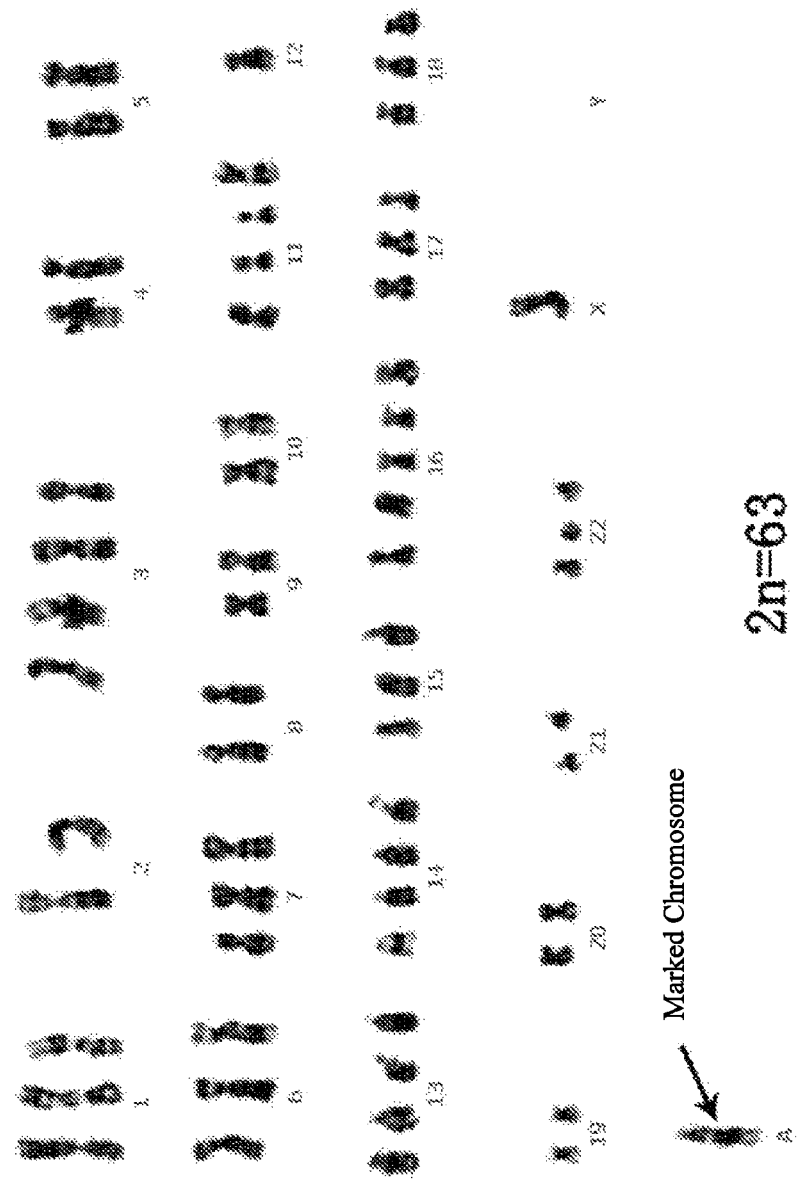

HUMAN HEPATOMA CELL LINE HLCZ01 AND USES THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a microbial animal cell field, and more particularly to a human hepatoma cell line and applications thereof.

Description of Related Arts

Human liver has many important physiological functions including: synthesizing and secreting large amounts of serum proteins, such as albumin and lipoproteins; synthesizing and transporting lipids coupling to proteins; detoxification; synthesizing and secreting bile; synthesizing sugar to regulate human blood sugar; decomposing amino acid to synthesize urea; activating vitamin; synthesizing and decomposing glycogen; synthesizing glutathione and metallothionein, and other functions.

With the progress of biotechnology, the gene recombination and cell fusion technology can produce more useful biological products. The animal cell culture technology is even more important. Based on that the liver has more physiological functions than other organs, including the functions of synthesizing and secreting the large amounts of cytoplasmic proteins, the ability to synthesize albumin and lipoproteins, the ability to transport lipid, urea, glycogen, and glutathione, and the stronger metabolism ability, researchers have more interested to use the liver cell culture technology to produce the above useful biological products. Therefore, in order to explore the functions of the liver and produce related biological products, the liver cell culture technology is urgently needed. However, cultivation techniques are not satisfactory at present for maintaining hepatocytes (normal liver cells) capable of producing plasma proteins during cultivation periods. Normal human hepatocytes are extremely difficult to obtain due to their rapid decrease in viability following autopsy.

Additionally, the human liver is one of few organs in adults capable of regeneration. However, replicative cultures of adult human hepatocytes have never been adequately established, as these cells have a very limited lifespan when put into cell culture.

Some existing liver cell lines are derived from a non-human source or some sources having significant difference with human hepatocytes, so the existing liver cell lines cannot be widely used. Currently, some liver cell lines are derived from experimental animals, such as rat (Tsao et.al, Exp. Cell Res, 1984, 154:38-52; Enat et al., Proc. Natl. Acad. Sci., USA, 1984, 87:1411-1415), and some are delivered from liver epithelial cells in rat, which are cultured based on serum free medium (Chessebeuf and Padieu, InVitro, 1984, 20:780-795; Enat et al., Proc. Natl. Acad. Sci., 1984, 81:1411-1415). Rat liver cells have been transformed by transfection with SV40 DNA (Woodworth et al., Cancer Res., 1987, 46:4018-4026; Ledley et al., Proc. Nat. Acad. Sci. USA, 1987, 84:5335-5339). Those cells are not suitable for the study of human drug metabolism or hepatocarcinogenesis because of xenobiotic metabolism differences between rat and human liver cells.

In addition, related reports which introduces the asexual reproduction technology for the human liver cells have been introduced (Kaighn and Prince, Proc. Nat. Acad. Sci., 1971, 68:2396-2400), and the long-term cultivation of the human fetal livers have also been established (Salas-Prato, M. et al., In Vitro Cell Dev. Biol., 1988, 24:230-238; Sells, M. A. et al., In Vitro Cell Dev. Biol., 1985,21:216-220). Since the metabolism between the fetal liver cells and adult liver cells are different, the fetal liver cells cannot be used for studying the formation of tumor and the application of toxicology. The adult liver cells are more suitable for studying the formation of tumor and the application of toxicology.

In order to find an alternative model as a study mode for liver cells, researchers have created cell lines derived from the liver cancer, which have the same function as normal hepatocytes (such as the function of the secretion of albumin). Currently, a variety of hepatoma cell lines have been established. (e.g., Knowles et al., U.S. Pat. No. 4,393,133, issued Jul. 12, 1983; Knowles B. B. et al., Science, 1980, 209:497-499; Monjardino J. and Crawford E., Virology, 1979,96:652-655; Park J. G. et al., Int. J. Cancer, 1995, 62:276-282; Fuand Cheng, Antimicrobial Agents and Chemotherapy, 2000, 44 (12) :3402-3407), such as that the U.S patent of the hepatoma cell line HepG2(U.S. Pat. No. 4,393,133). Furthermore, studies related to the HepG2 have been reported. (Kelly et al., In Vitro Cell, and De. Biol, 1989, 25:217-222; U.S. Pat. No. 5, 290,684; and Darlington et al., In Vitro Cell, and Dev. Biol., 1987, 2-3:349-354). In addition, hepatoma cell line Huh7 has been established by Nakabayashi (Cancer Research, 1982, 42:3858-3863). According to the existing published literatures, the existing hepatoma cell lines include, but are not limited to: HLF (Okayama University, medical school :1975), HLE, c-1 (Okayama University, medical school: 1975), HuH-6clone5 (Okayama University, medical school: 1976), HuH-7 (Okayama University, medical school: 1979), C-HC-4 (Hokkaido University, school of medicine: 1979), HCC-M (Keio University, school of medicine: 1980), JHH-1 (The Tokyo Jikei University School of Medicine: 1980), JHH-2 (The Tokyo Jikei University School of Medicine: 1982), JHH-4 (The Tokyo Jikei University School of Medicine: 1983), KIM-1 (Kurume University, school of medicine: 1983), JHH-5 (The Tokyo Jikei University School of Medicine: 1984), JHH-6 (The Tokyo Jikei University School of Medicine: 1984), OHR (Showa University, school of medicine: 1985), KMCH-1 (Kurume University, school of medicine: 1985), KMG-A (Kurume University, school of medicine: 1985), JHH-7 (The Tokyo Jikei University School of Medicine: 1986), JHC-1 (The Tokyo Jikei University School of Medicine: 1986), KYN-1 (Kurume University, school of medicine: 1986), KYN-2 (Kurume University, school of medicine: 1987), HCC-T (Keio University, school of medicine: 1986), HPT-NT/D3 (Kyushu University, faculty of medicine: 1986), Hep-tabata (Mie University, Faculty of Medicine: 1986), HuCC-T1 (Toyama Medicine and Pharmaceutical University, faculty of medicine: 1987), HuH-28 (Okayama University, medical school: 1987). The relevant data can be found in HUMAN CELL, Vol. 1, No. 1, p. 106-126, 1988.

There have been a lot of research reports using the bioreactor to culture liver cells in order to manufacture artificial liver. The artificial technology has dramatically been improved in the progress of kidneys, heart and lung transplant. The use of artificial liver and other techniques to long-term remain the functions of liver have been reported (e.g., Anand A. C., Indian J. Gastroenterol., 2003,22 Supp12: S69_74; Ueda et al., ASAIOJ, 2003,49 (4) :401-6; Tilles et al., J. Hepatobiliary Pancreat. Surg., 2002,9 (6) :686-96; Metab. Brain Dis., 2005,20 (4) :327-35; and Park and Lee, J. Biosci Bioeng., 2005,99 (4) :311-9). Liver assist devices (LAD) have been described previously (e.g., Lu et al., Tissue Eng., 2005, 11 (11-12) :1667-77; Pless and Sauer, Transplant Proc., 2005,37 (9) :3893-5; Millis and Losanoff, Nat. Clin. Pract. Gastroenterol Hepatol., 2005,2 (9) :398-405; and George J., J. Assoc. Physicians India, 2004, 52:719-22).These liver assistance devices are often used in transplant surgery. For example, an artificial liver and liver assistance devices are able to make fulminant hepatic failure patients keep away and calm before surgery, and make the patients more stable after the transplant surgery, and more particularly when the patents have no response to perfusion, the artificial liver and the liver assistance devices may serve as a substitute for transplant in certain circumstances. In order to make better use of bio-artificial livers and liver assistance devices, the small and compact in size bioreactor are needed. Therefore, the cells cultured in the bioreactor are required to produce sufficient liver-specific proteins. Researchers have successfully cultured liver cells HepG2 in the above mentioned liver assistance devices cells to produce an anti-apoptotic protein Bcl-2 (Terada S., J. Biosci. Bioeng., 2003, 95 (2) :146-51).

Liver cancer is a common cancer, wherein most of the liver cancers are caused by hepatitis viruses, such as hepatitis B virus (HBV) and hepatitis C virus (HCV). Currently, no effective therapy is able to cure this disease. HCV infection is a major human infectious disease, and there is no effective vaccine to prevent HCV infection. There have been parts of evidences introduced to prove an importance of the cellular immune in the clearance of hepatitis virus, but the antibody-mediated antiviral responses within the patients' bodies are not defined. Most of antibodies in the patient's body can neutralize viral antigens, but the levels and concentration of neutralized antibodies within the serum are unknown, such that the study of the neutralizing antibodies is limited due to the lack of the cell culture model and animal model supporting virus infection.

Despite some of the liver cell lines are derived from the human hepatoma cells, most of these existing cell lines are poorly differentiated and the functions thereof are not perfect. To our knowledge, there is no liver cell line which is able to support HBV and HCV infection, such that the development and application of antiviral drugs are limited. Although, some research teams use primary human hepatocytes and detect low-level replication of HCV therein, but there is no liver cell line supporting the strong replication of wild-type HCV. (Tagawa M. et al., J. Gastroenterol Hepatol, 1995, 10:523-527; Ito T. et al., J. Gen. Virol., 1996, 77 (Pt.5):1043-1054; Ito T et al., Hepatology, 2001, 34:566-572). In 2005, several groups reported the success of cell culture system that supports the lifecycle of one particular strain, JFH1, a genotype 2a isolate of HCV (Wakita T. et al., Nat. Med., 2005,11 (7) :791-796; Zhong J. et al., PNAs, 2005,102 (26) :9294-9; Lindenbach B. D. et al., Science2005, 309 (5734) :623-6).

Currently, the only successful animal model to support HCV infection is the chimpanzee (Lanford R. E. et al., Virology, 2002, 293:1-9). This animal model has the advantages of showing the lifecycle of the virus, although the pathology is different than the human with virus infection (Alter M. J. et al., N. Eng. J. Med., 1999, 341:556-562; Bassett S. E. et al., J Virol, 1998, 72:2589-2599), and this model provided tremendous knowledge about the host immune responses to HCV infection. The maximum limitation of the above mentioned model is that the source of chimpanzee is less and the cost is extremely expensive. Tupaia is a small animal which is close to the primates, so it is easy to adapt to the laboratory environment. Based on some studies, Tupaia is able to be infected by a variety of human viruses, including hepatitis virus (die Z. C.et al., Virology, 1998, 244:513-520).

Transgenic mice that express HCV core protein have been used to study the liver pathology and carcinogenesis (Lemon S. M. et al., Trans. Am. Clin. Climatol. Assoc., 2000, 111:146-156). Most of the transgenic mice cannot show the toxicity to hepatocytes, while one transgenic animal showed lymphocytic infiltration and hepatocyte necrosis (Zhao X. et al., J. Clin. Invest, 2002,109:221-232), and another two models suffer from the steatosis and hepatoma (Moriya K. et al., J. Gen. Virol, 1997,78 (Pt.7) :1527-1531; Moriya K. et al., Nat. Med., 1998,4:1065-1067). The HBV transgenic mice are able to be used for studying the mechanism of immune response to HBV (Chisari F. V. et al., Science, 1985, 230:1157-1160; Chisari F. V. et al., Hepatology, 1995, 22:1316-1325). However, transgenic models are not yet widely used in the studies on HCV immunology. One inherent problem using transgenic mouse models is host immune tolerance to viral proteins.

According to the above mentioned published research reports, liver cell lines and animal models for HBV and HCV are extremely needed. The potential applications of these cell lines include, but are not limited to: screening and evaluating anticancer drugs; culturing HBV and HCV in a manner resembling the naturally occurring infection; screening and evaluating antiviral drugs; studying metabolic functions of hepatocytes.

SUMMARY OF THE PRESENT INVENTION

A main object of the present invention is to provide a human hepatoma cell line HLCZ01 which is a well-differentiated cell line, wherein the human hepatoma cell line HLCZ01 can be cultured in vitro and has liver functioning abilities. The human hepatoma cell line HLCZ01 of the present invention can be used to screen and evaluate anti-tumor drugs; propagate (culture) but not limited to HBV and HCV in a manner resembling the naturally occurring infection; screen and evaluate antiviral drugs; and study hepatocytes metabolism. HBV and HCV robustly replicate in the human hepatoma cell line HLCZ01.

Accordingly, in order to accomplish the above mentioned object, a human hepatoma cell line HLCZ01 according to a preferred embodiment of the present invention is obtained, wherein the human hepatoma cell line HLCZ01 has been deposited in the China Center for Type Culture Collection (CCTCC), and the accession (deposit) number is CCTCC NO: C201309, and the address of the institution (CCTCC) is located in Wuhan University, China, and the preservation date is Jan. 17, 2013, and the human hepatoma cell line is named as HLCZ01.

Accordingly, the number of the chromosomes within the human hepatoma cell line HLCZ01 is preferably 54 to 63.

After karyotype analysis of chromosome G band, the human hepatoma cell line HLCZ01 shows the phenomenon of heteromorphic chromosomes and a marker chromosome appears in the karyotype.

The human hepatoma cell line HLCZ01 not only contains hepatocyte specific genes ALB and AAT, but also expresses hepatocyte specific proteins ALB and AAT. According to the above mentioned human hepatoma cell line HLCZ01, the human hepatoma cell line HLCZ01 is a well-differentiated cell line. The human hepatoma cell line HLCZ01 can be infected by hepatitis viruses, such that hepatitis viruses can be, but not limited to hepatitis B virus (HBV) and/or hepatitis C virus (HCV), including various genotypes of HCV and various genotypes of HBV. HBV and HCV can replicate robustly in the human hepatoma cell line HLCZ01 of the present invention.

Accordingly, the human hepatoma cell line HLCZ01 of the present invention is a cell model which is able to support hepatitis viruses infection, and the hepatitis viruses includes but not limited to hepatitis B virus and hepatitis C virus (including various genotypes of hepatitis C virus and various genotypes of hepatitis B virus). The human hepatoma cell line HLCZ01 of the present invention is able to support the entire lifecycle of HBV and HCV. HBV and HCV can infect and replicate in the human hepatoma cell line HLCZ01 of the present invention to simulate the natural infection of hepatitis viruses.

Accordingly, the human hepatoma cell line HLCZ01 of the present invention can be used to establish animal models for supporting virus infection. Preferably, the hepatitis viruses can be, but not limited to hepatitis B virus and/or hepatitis C virus. Specifically, the human hepatoma cell line HLCZ01 of the present invention can be used in non-human animal models, and the human hepatoma cell line HLCZ01 not only can be implanted into animals (e.g. mice), but also can be used to build an animal model supporting virus infection. The human hepatoma cell line HLCZ01 of the present invention is provided to build an animal model to study liver pathology and hepatitis viruses. As mentioned above, since the human hepatoma cell line HLCZ01 can support entire lifecycles of HBV and HCV, the human hepatoma cell line HLCZ01 can reproduce key pathological process of hepatitis B and hepatitis C. Therefore, the animal models implanted with the human hepatoma cell line HLCZ01 of the present invention can be used to study the human antiviral responses to HBV and HCV.

Accordingly, the human hepatoma cell line HLCZ01 of the present invention not only can be used as a cell model for supporting hepatitis virus infection, but also can be used to establish an animal model implanted with HLCZ01 cells supporting viral infection, which facilitate the development of antiviral drugs (including viral vaccines and other auxiliary agents). Therefore, the human hepatoma cell line HLCZ01 of the present invention is also able to be applied in the preparation, screening or evaluating the anti-hepatitis viral drugs. The above described hepatitis viruses include but not limited to HBV and/or HCV.

Accordingly, the human hepatoma cell line HLCZ01 can be cultured in the culture medium outside the living body, and can be used to do the carcinogenic and teratogenic researches. Based on the chemical carcinogenicity studies, the human hepatoma cell line HLCZ01 can be used in preparation, screening or evaluating the antitumor drugs.

Accordingly, the human hepatoma cell line HLCZ01 has important functions and features of the liver to transfer ammonia into urea. The function for transferring ammonia into urea renders HLCZ01 to be a useful tool to manufacture artificial liver and ancillary liver equipment, which is able to be used for clinic or researches. Therefore, the human hepatoma cell line HLCZ01 of the present invention also can be used in the preparation of artificial livers.

According to the above mentioned application, the human hepatoma cell line HLCZ01 of the present invention can be used to study hepatocyte metabolism (such as evaluating the metabolic activation of compounds in the liver), metabolic functions, lifecycles of hepatitis viruses in hepatocytes, and human parasites. The human hepatoma cell line HLCZ01 can also be used to explore the functions of exogenous gene through transferring exogenous gene into the cells. Due to that the human hepatoma cell line HLCZ01 of the present invention can express cytochrome P450, CyP1A1, CyP1B1 and CyP2C9 proteins, the human hepatoma cell line HLCZ01 can be applied in homologous cell experiments, such as drug metabolism studies.

Compared with the prior art, the advantages of the present invention are to provide a novel human hepatoma cell line HLCZ01 which is not only a well-differentiated hepatoma cell line, but also can be cultured and passaged in vitro. The human hepatoma cell line HLCZ01 has important functions and features of human liver, which can convert the ammonia into urea, and express cytochrome P450, CyP1A1, CyP1B1 CyP2C9 proteins. More importantly, the human hepatoma cell line HLCZ01 can be infected by hepatitis viruses. Moreover, HBV and HCV can infect and replicate robustly in HLCZ01 cells. Due to the special properties of the human hepatoma cell line HLCZ01 of the present invention, the human hepatoma cell line HLCZ01 of the present invention can be widely used in the development, preparation, screening and evaluating the anti-virus and anti-tumor drugs, and can be used to produce a variety of clinical biological products and bio-artificial livers. The hepatoma cell line HLCZ01 is a better tool to study liver metabolism and pathogenesis of liver diseases compare with other liver cell lines.

The human hepatoma cell line HLCZ01 of the present invention is preserved in China Center for Type Culture Collection (CCTCC), with the address in Wuhan University, in China, and the accession no. is CCTCC NO: C201309, and the preservation date is on Jan. 17, 2013.

Additional advantages and features of the invention will become apparent from the description which follows, and may be realized by means of the instrumentalities and combinations particular point out in the appended claims.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE FIGURES

Referring to FIG. 4, HCV-infected HLCZ01 can be detected as the viral protein NS5A is demonstrated inside the cells, wherein a left diagram of the FIG. 4 shows viral-infected cells detected by anti-HCV NS5A antibody, and a medium diagram of the FIG. 4 shows cell nuclei which have been stained by DAPI, and a right diagram of the FIG. 4 is a merger including the left and medium diagram of the FIG. 4.

FIG. 7 shows that HLCZ01 cells are susceptible to HBV and HCV infection. The cells were stained with anti-HBcAg antibody and anti-HCV NS5A antibody respectively. HBV core antigen and HCV NS5A protein can be detected within the same HLCZ01 cell, wherein a NS5A diagram of FIG. 7 shows that HCV NS5A protein can be detected in HLCZ01 cells, and a HBcAg diagram demonstrates that HBV core antigen can be detected in the HLCZ01 cells, and a DAPI diagram of FIG. 7 shows cell nuclei which have been stained with DAPI, and a merge diagram is combined the NS5A, HBcAg, DAPI, and Merge diagram of FIG. 7.

FIG. 13 is the result of Karyotype analysis for human hepatoma cell line HLCZ01 (2n=54).

FIG. 14 is the result of Karyotype analysis for human hepatoma cell line HLCZ01 (2n=59).

FIG. 15 is the result of Karyotype analysis for human hepatoma cell line HLCZ01 (2n=63).

DETAILED DESCRIPTION OF THE PREFERRED EMBODIMENT

Figure 1:
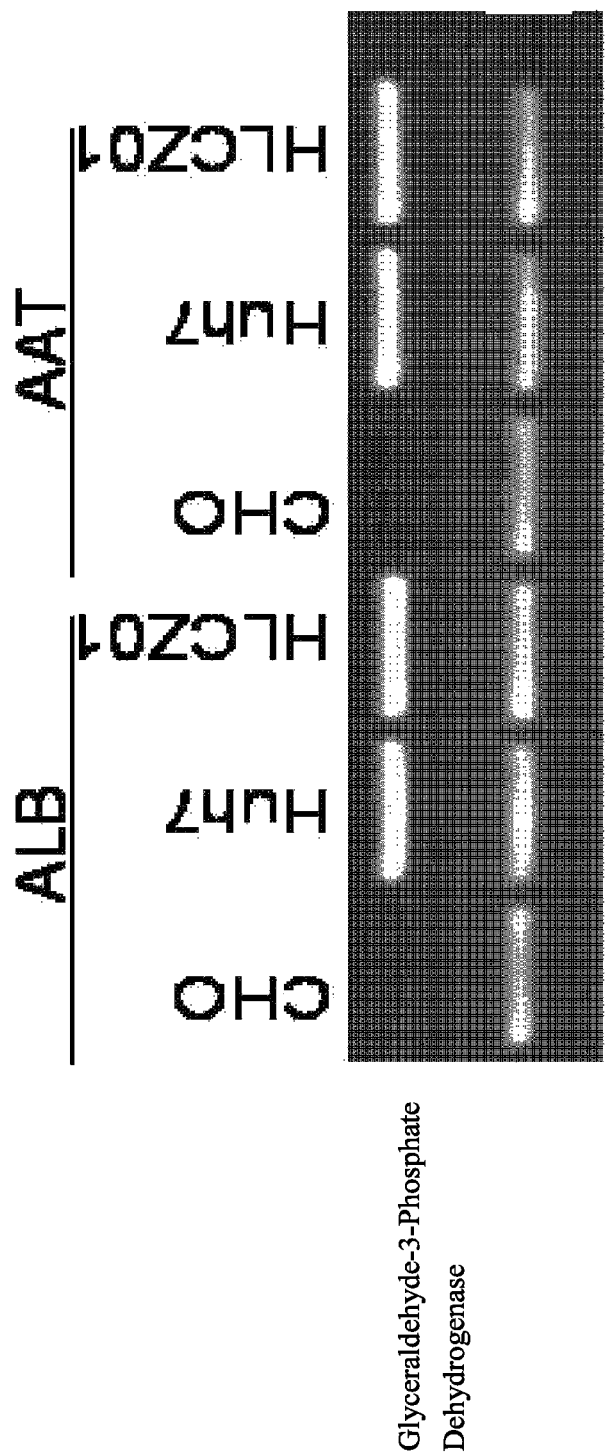
FIG. 1 is an electropherogram showing that HLCZ01 cells express liver-specific genes ALB and AAT detected by RT-PCR.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

The following embodiments, if no special instructions, are accomplished in conventional methods. The experimental materials and biological agents used in the following embodiments, if no special instructions, are available from conventional commercially reagents. The quantitative experiments in the following embodiments are repeated three times to obtain average results.

Experimental materials and reagents used in the following embodiments:

(1) Cell Culture: human hepatoma cell line HLCZ01 (persevered), Huh7.5 cells (donated by Professor Charles Rice laboratory of the Rockefeller University), HCVcc (JFH1 virus supernatant, and pJFH1 materials are donated by Professor Takaji Wakita Lab of National Institute of Infectious Diseases, in Japan), 100 mm cell culture plates (Costar Corporation), 60 mm cell culture plates (Costar Corporation), 6-well cell culture plates (Costar Corporation), DMEM medium (Invitrogen Corporation), penicillin and streptomycin (Invitrogen Corporation), glutamine (Invitrogen Corporation), goat serum (Invitrogen Corporation), trypsin (Invitrogen Corporation), non-essential amino acids (Invitrogen Corporation), 1×PBS (Hyclone Company);

(2) Total cellular RNA extraction: TRIzol (Invitrogen Corporation), isopropanol (Shanghai Biological Corporation), anhydrous ethanol (Shanghai Biological Corporation), DEPC (Shanghai Biological Corporation);

(3) Reverse Transcription PCR and Real Time PCR: RT-PCR test kit (Invitrogen Corporation), SYBR Premix Ex Taq (Taraka company), 200 μL PCR eight-joints tube (Eppendorf Corporation);

(4) The total cellular protein extraction: RIPA lysis buffer (Thermo Corporation), protease inhibitor (Merck company), and protein concentration determination reagent (Bio-Rad company);

(5) Western Blot: PVDF membrane (Bio-Rad Corporation), anti-ALB antibody (SANTA CRUZ), anti-AAT antibody (SANTACRUZ), anti-HCV NS5A antibody (gifts from University of Florida), secondary anti-goat or anti-mouse IgG (HRP) (Invitrogen Corporation), Western Blot chemiluminescent substrate (Thermo Corporation), Western Blot exposing machine (Keda company);

(6) Immunofluorescence: slide glass and cover glass (SPI Supplies Corporation), immunohistochemical pen (ZL1-9305, PAPPen), 1×PBS (Hyclone company), goat serum (Invitrogen Corporation), mouse anti-HCV NS5A antibody (homemade), secondary goat anti-mouse IgG (FITC) (Invitrogen Corporation), DAPI (Invitrogen Corporation).

A human hepatoma cell line HLCZ01 according to a preferred embodiment of the present invention is obtained, wherein the human hepatoma cell line HLCZ01 has been deposited in the China Center for Type Culture Collection (CCTCC), and the accession number is CCTCC NO: C201309, and the address of the institution (CCTCC) is located in Wuhan University, China, and the preservation dated is on Jan. 17, 2013, and the human hepatoma cell line is named as HLCZO1.

The establishment and culturing methods for HLCZ01 cell line:

1. Take a fresh surgical specimen tissue from tumor tissue from one male patient suffering from liver cancer through liver resection. The specimen tissue is washed by PBS, cut into a small piece having the size of 1 $mm^3$, and placed in a 100 mm petri dish which has been treated with collagen. Then, 8 ml of fresh medium is added into the petri dish, and epidermal growth factor at the concentration of 10 ng/ml is also added into the medium.

2. Change the medium after the first 2 days, and then change the medium every 3 days.

3. Observe cells grew in the petri dishes until the cell clones appeared, and the cell clones are washed by PBS. 0.25% trypsin is dropped on the cell clones. The cell clones are placed in the incubator for one minute. Then take out the cell clones from the incubator and the fresh medium with absorbed cell clones is extracted by a pipettor, and the absorbed cell clones are transferred and cultured in a 12-well plate.

4. Transfer the cells to a 6-well plate after the absorbed cell clones grow all over the 12-well plate, and then transfer the cells to a 100 mm petri dish after the cells grow all over the 6-well plate.

5. Inoculate $1\times10^7$ cells under the skin of NOD-SCID mice, such that tumor grows within the NOD-SCID mice after 45 days. The tumor is removed and cultured in accordance with the above mentioned cultivation method to obtain HLCZ01 cells.

The human hepatoma cell line HLCZ01 of the present invention has hepatocyte specific genes ALB and AAT detected by RT-PCR, wherein the detected process is shown as follows:

The human hepatoma cell line Huh7, the human hepatoma cell line HLCZ01 of the present invention and Chinese hamster ovary cell line CHO (purchased by ATCC from the United States) are placed on the 6-well cell culture plates (300,000/well), each cell line occupies two wells of the 6-well cell culture plates. After culturing for 24 hours, one well from each cell line is taken to extract the total RNA by TRIZOL, and 1 μg of RNA reversely transcribed into cDNA. One μL of cDNA is used as a template for processing PCR. ALB and AAT genes are amplified, and the result of the amplification is shown in FIG. 1. As shown in FIG. 1, the human hepatoma cell line Huh7 and human hepatoma cell line HLCZ01 express the hepatocyte specific genes ALB and AAT, but not in non-hepatoma cell line CHO.

Figure 2:
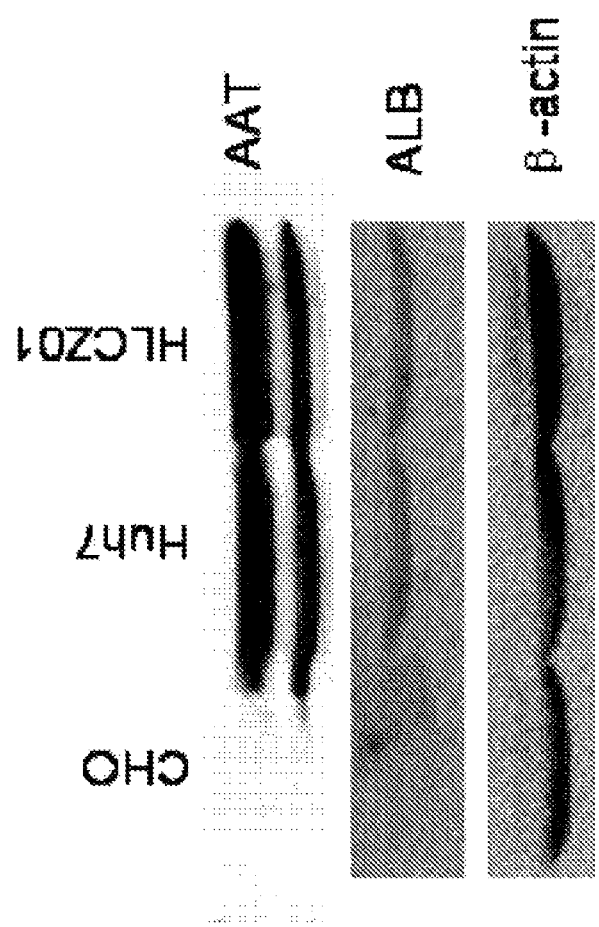
FIG. 2 is a Western Blot result demonstrating that HLCZ01 cells express liver-specific proteins ALB and AAT.

The human hepatoma cell line HLCZ01 of the present invention is able to express hepatocyte specific proteins ALB and AAT by Western Blot, and the process for Western blot is shown as follows:

The remaining three wells of the 6-well cell culture plate containing three kinds of cell lines, the human hepatoma cell line Huh7, the present invention of human hepatoma cell lines HLCZ01 and Chinese hamster ovary cell line CHO, are processed by cell lysis with RIPA Buffer, and the cell lysate is placed on ice for 15 minutes. The cell lysate is centrifuged at 13000 rpm for 15 minutes (4° C.) and the supernatant from the cell lysate is transferred into a new EP tube. The supernatant is detected by the Lowry method to measure the concentration of protein. Fifty microgram of protein is separated by polyacrylamide gel electrophoresis (SDS-PAGE), and the protein which has been processed through the polyacrylamide gel is transferred to a PVDF membrane. The HRP-labeled anti-ALB and anti-AAT antibodies are used to detect the ALB and AAT. The results are shown in FIG. 2. As shown in FIG. 2, the human hepatoma cell line Huh7 and HLCZ01 cell line are able to express ALB and AAT proteins, but CHO cell line cannot express these two proteins.

According to the above mentioned embodiment, the human hepatoma cell line HLCZ01 of the present invention not only contains hepatocyte specific genes ALB and AAT, but also expresses hepatocyte specific proteins ALB and AAT.

The human hepatoma cell line HLCZ01 of the present invention is processed by Karyotype analysis, and the karyotype analysis is reference to the U.S. animal cell line ATCC Karyotype analysis. Inspection cells are passaged, wherein P2, P4, and P7 generation cells (1000 metaphase cells) are processed by chromosome preparation respectively, and the frequency distribution for chromosome of P2, P4, P7 is calculated based on an ordinary karyotype. G band is observed with staining, and CCD imaging is analyzed through VideoTest-Karyo3.1 karyotype analysis software.

Figure 12:
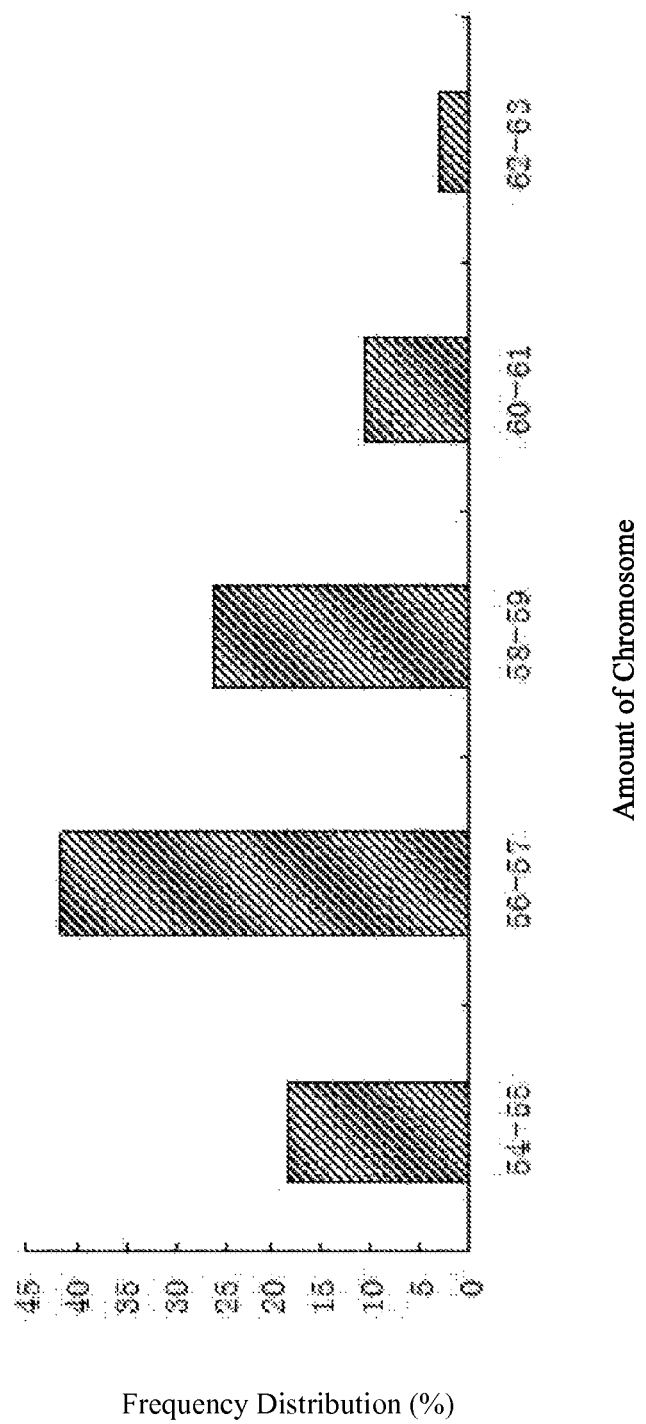
FIG. 12 is a chromosome frequency distribution chart for the human hepatoma cell line HLCZ01 after being processed Karyotype analysis.

According to the human hepatoma cell line HLCZ01 of the preferred embodiment of the present embodiment, the karyotype analysis shows that the number of chromosomes is 54 to 63 and the frequency distribution after the karyotype analysis is shown in FIG. 12.

According to the human hepatoma cell line of the preferred embodiment of the present invention, after the human hepatoma cell line HLCZ01 is processed by Karyotype analysis with chromosome G band stain, and, as a result, the existence of chromosomes dissimilation appears, and a marked chromosome appears within the karyotype. The three most typical sets of chromosomes, 2n=54, 2n=59, 2n=63, are illustrated as examples, and the karyotype analysis results are shown in FIG. 13 to FIG. 15. As shown in FIGS. 13 to 15, karyotypes analysis results have a marked chromosome.

Application Embodiment 1: HLCZ01 can be Infected by Hepatitis C Virus

1. The human hepatoma cell line HLCZ01 cells and Huh7.5 cells are placed on the 6-well cell culture plate (200,000/well). After 24 hours, the medium is replaced with medium containing 2% FBS, and the cells are infected by HCV. The medium is changed after 24 hours. Huh7.5 cells and human hepatoma cell line HLCZ01 are cultured for 1 day, 2 days, 3 days and 6 days respectively, and TRIZOL is used to extract total RNA from the above mentioned two cell lines at different time points after virus infection. One microgram of the total RNA is reversely transcribed into cDNA, and 1 μL of cDNA are used as templates for processing quantitative PCR. HCV RNA levels in these two cells are detected by real-time PCR, as shown in FIG. 3.

Figure 4:
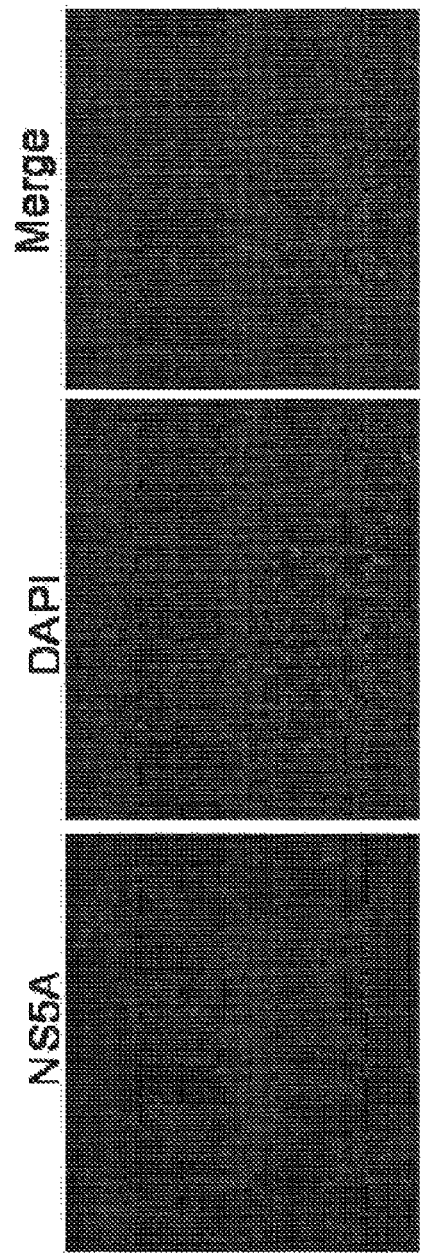
FIG. 4 shows that HLCZ01 cells are susceptible to HCV. HCV-infected HLCZ01 cells were stained with anti-HCV NS5A antibody by immunofluorescence according to the first embodiment of the present invention.

2. At 3 days postinfection, the above mentioned HCV-infected HLCZ01 cells are placed on the cover glass within the 60 mm petri dish and are continuously cultured for another three days. 1×PBS is used for washing the cover glass twice and the ice-acetone is used to fix HLCZ01 cells growing on the cover glass for 8 minutes. HLCZ01 cells growing on the cover glasses are washed by the 1×PBS for three times, and each time is five minutes. The goat serum is used to block the background of the cells grown on cover glass at room temperature for 30 minutes and mouse anti-NS5A antibody is used to process immunofluorescence analysis for one hour. 1×PBS is used to wash the cells for three times and the FITC-labeled secondary antibody is added for one hour. After that, 1×PBS is used for washing the cells for another three times and DAPI is used to seal the cover glass with HLCZ01 cells. Finally HLCZ01 cells growing on cover glass are observed under a fluorescence microscope, as shown in FIG. 4. Referring to FIG. 4, HCV-infected HLCZ01 can be detected as the viral protein NS5A is demonstrated inside the cells, wherein a left diagram of the FIG. 4 shows viral-infected cells detected by anti-HCV NS5A antibody, and a medium diagram of the FIG. 4 shows cell nuclei which have been stained, and a right diagram of the FIG. 4 is a merger including the left and medium diagram of the FIG. 4.

According to the preferred embodiment of the present invention, after the human hepatoma cell line HLCZ01 is infected by HCV, HCV RNA could be detected by fluorescence quantitative PCR, and the viral protein in HCV-infected HLCZ01 cells could be detected by the immunofluorescence process, such that the HLCZ01 is further confirmed to have the ability to be infected by HCV. Moreover, HLCZ01 can be infected by various genotypes of HCV produced both in cell culture and clinically. Based the above mentioned knowledge, the human hepatoma cell line HLCZ01 of the present invention is able to be a cell model supporting the HCV. Human hepatoma cell line HLCZ01 of the present invention not only can be used for animal models for supporting the HCV, but also can be used for the preparation, screening or evaluating the anti-HCV drugs.

Figure 3:
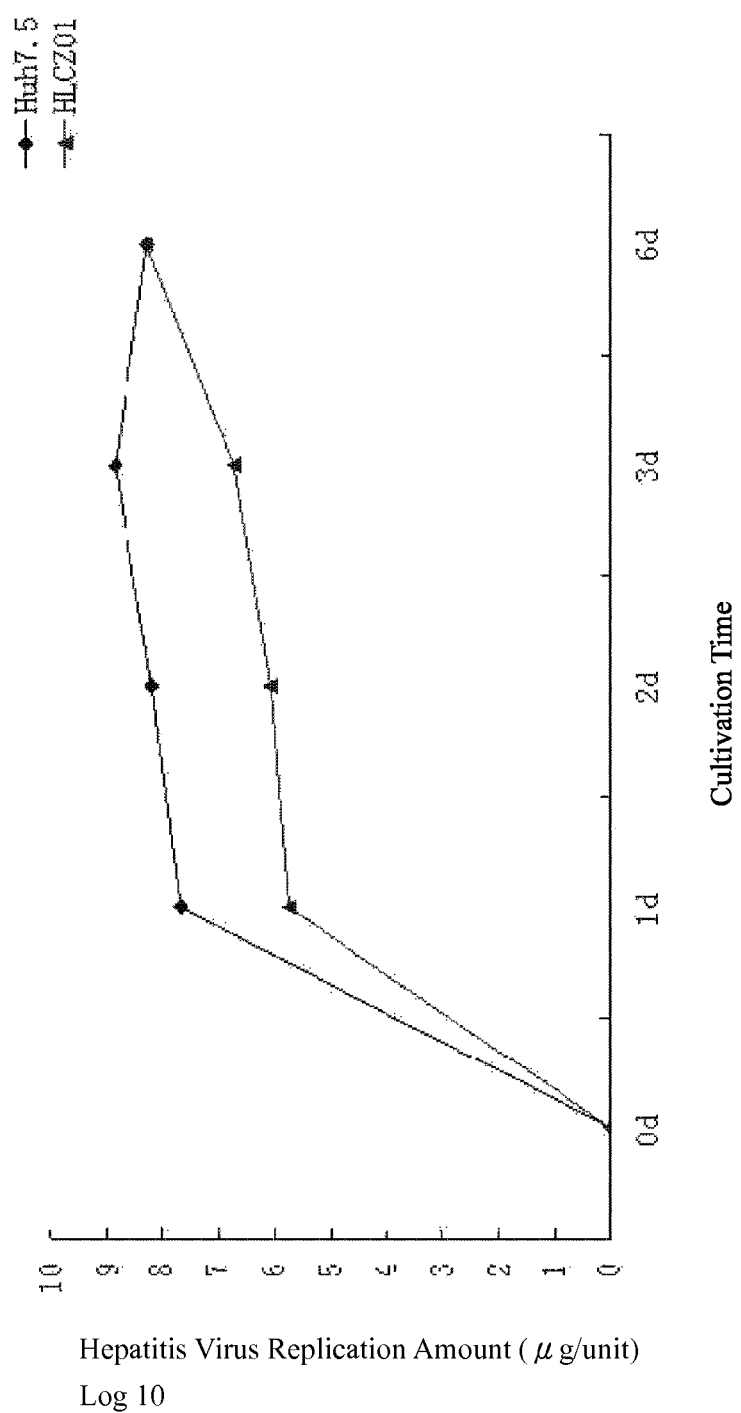
FIG. 3 is a variation curve for an amount of HCV with respect to cultivation time (days), illustrating a human hepatoma cell line HLCZ01 being infected by the HCV according to the first embodiment of the present invention.

Referring to FIG. 3 and FIG. 4 of the drawings, the human hepatoma cell line HLCZ01 of the present invention is able to be a cell model supporting hepatitis virus (above described HCV).

Figure 8:
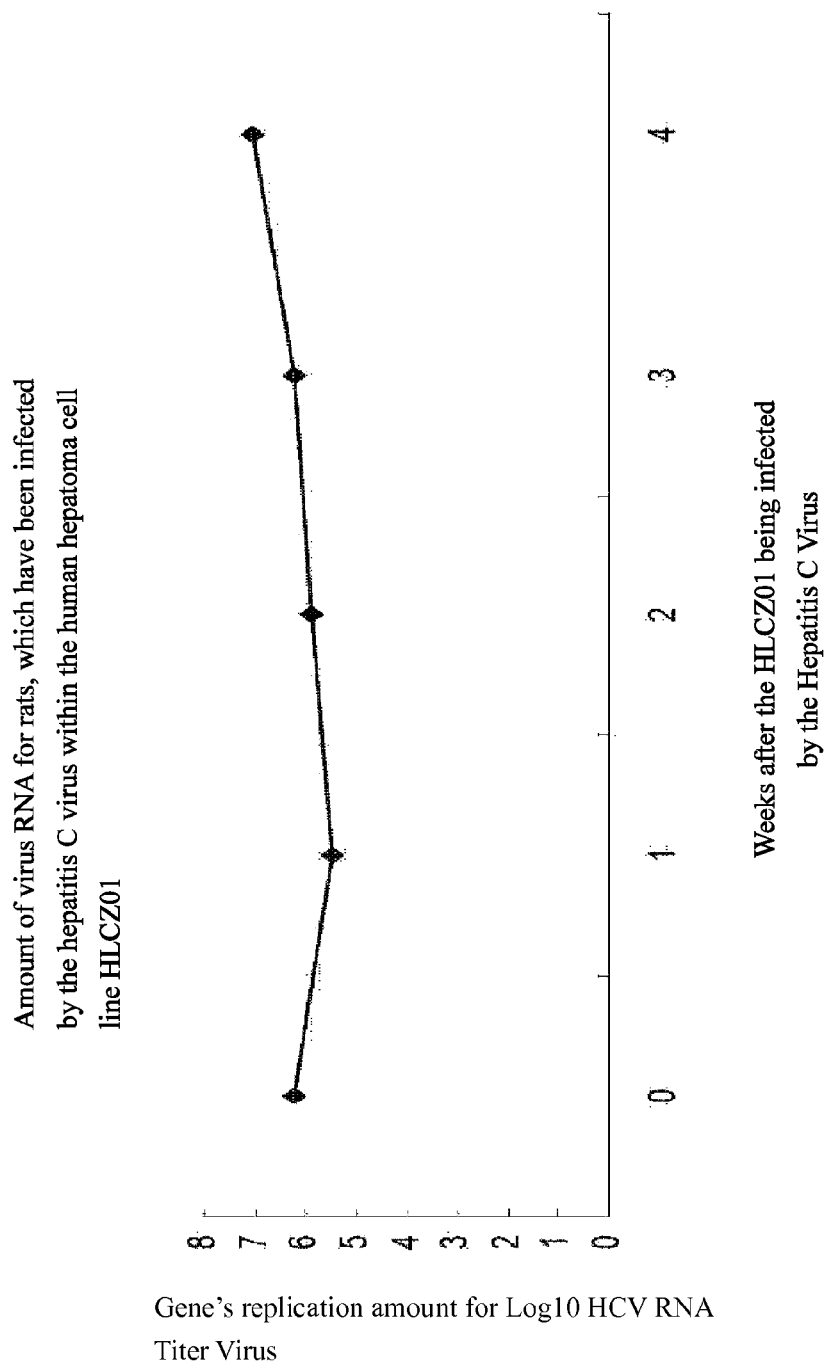
FIG. 8 is a variation curve for humanized mice implanted with the human hepatoma cell line HLCZ01 being infected by the HCV according to the above first embodiment of the present invention, illustrating the amount of virus in the sera of mice with respect to time(weeks).

Referring to FIG. 8 of the drawings, the human hepatoma cell line HLCZ01 can be used for animal models for supporting hepatitis C virus. FIG. 8 shows the HCV levels in the sera of humanized mice implanted with HLCZ01 cells after virus infection with respect to time (weeks). When the mice implanted with the human hepatoma cell line HLCZ01 are infected with hepatitis C virus, HCV level in the sera of mice is changed due to the infection time as shown in FIG. 8.

Figure 10:
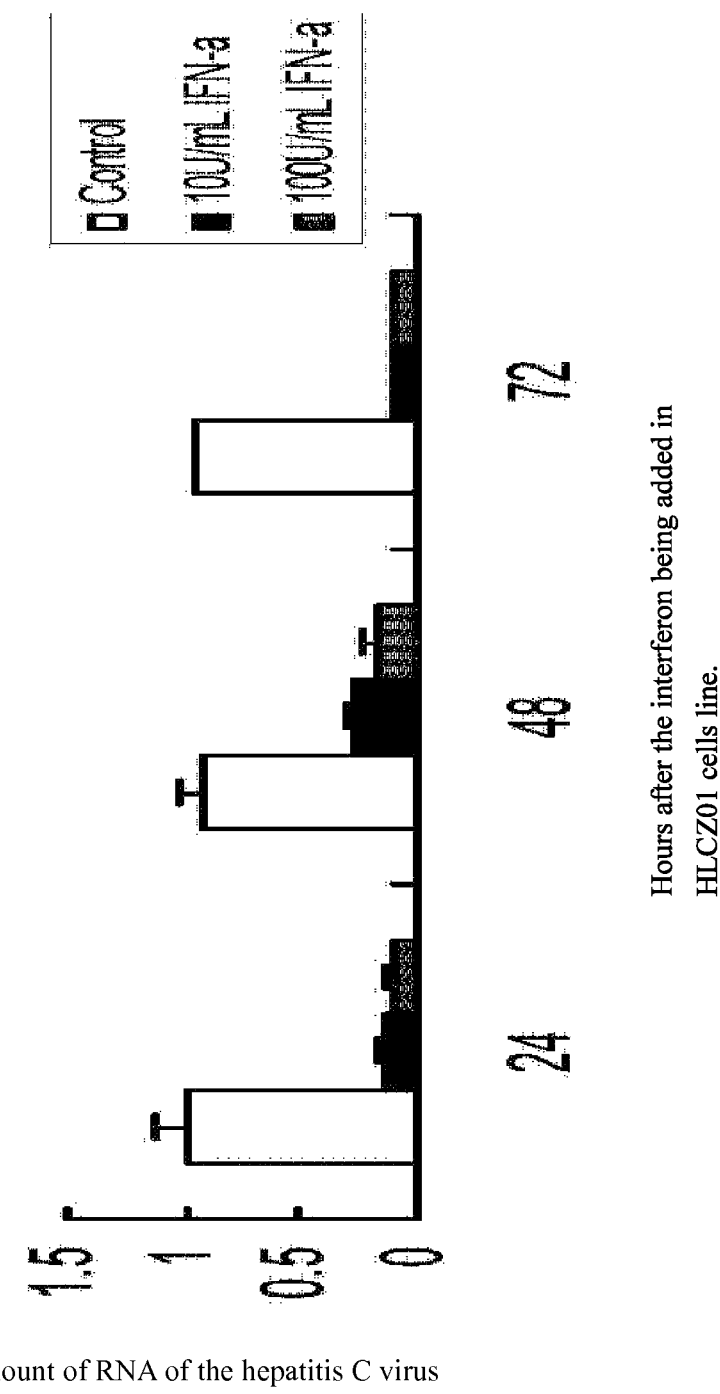
FIG. 10 is a column diagram for the human hepatoma cell line HLCZ01 according to the above first embodiment of the present invention, illustrating the amount of HCV with respect to the amount of interferon used and time (hours).

According to the human hepatoma cell line HLCZ01 of the present invention, the human hepatoma cell line HLCZ01 can also be used for the preparation, screening or evaluating anti-HCV drugs. After the human hepatoma cell line HLCZ01 has been infected by hepatitis C virus, α-interferon which has been used to cure the hepatitis C is able to reduce the amount of virus in HCV-infected HLCZ01 cells, as shown in FIG. 10. FIG. 10 demonstrated that the amount of HCV in HCV-infected HLCZ01 cells is changed after α-interferon is used to treat HCV-infected HLCZ01 cells, wherein FIG. 10 illustrates the change of the amount of virus in HCV-infected HLCZ01 cells with respect to the doses of α-interferon and time (hours). Therefore, the human hepatoma cell line HLCZ01 of the present invention can be used for the preparation, screening or evaluating the anti-HCV drugs.

Application Embodiment 2: HLCZ01 is Infected by Hepatitis B Virus

Figure 5:
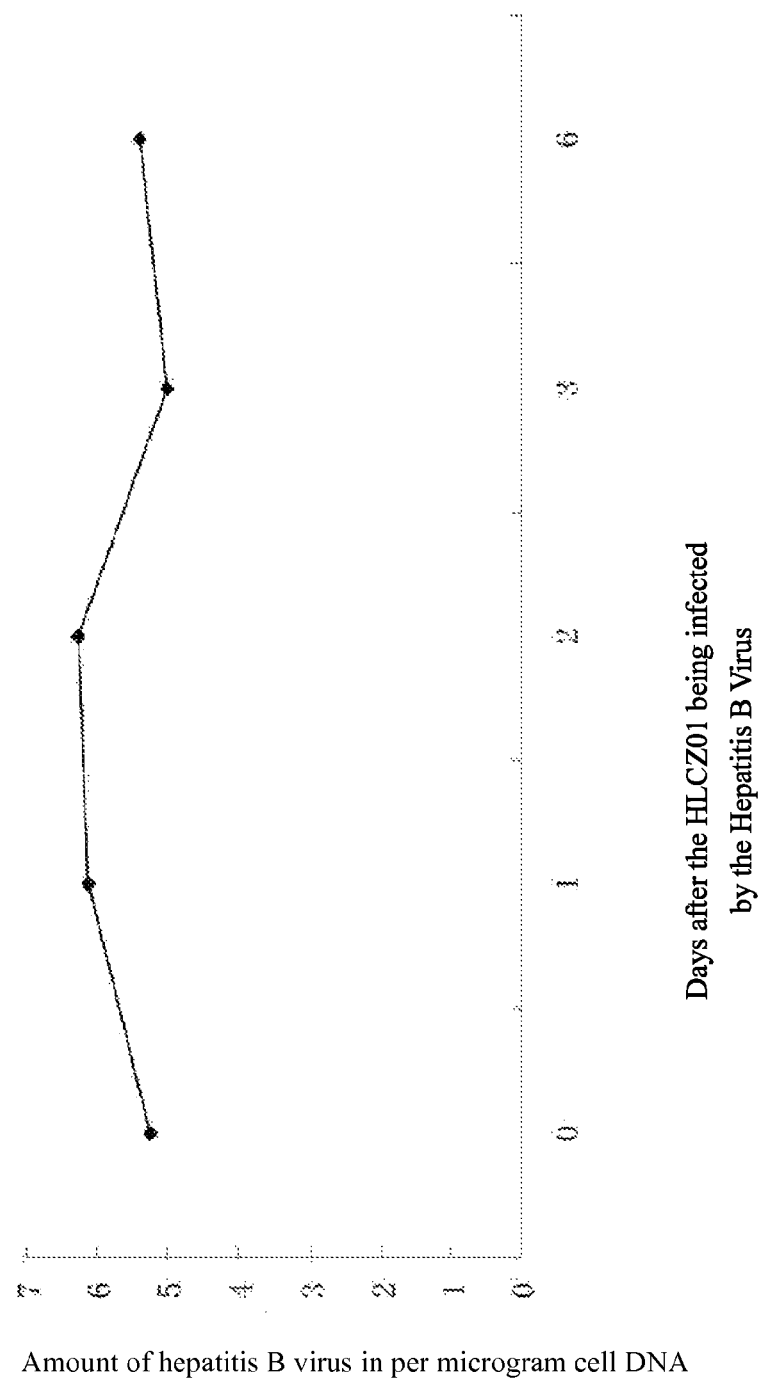
FIG. 5 shows a quantitative PCR results for the human hepatoma cell line HLCZ01 being infected by HBV from HepaG2.2.15 cells according to the second embodiment of the present invention.

The human hepatoma cell line HLCZ01 is placed on the 60 mm culture plate. After 24 hours, the medium (DMEM medium) is replaced to the mixture of a supernatant of HepaG2.2.15 cells with a complete medium (1:1 by volume ratio), and then the human hepatoma cell line HLCZ01 is continuously cultured. The cells were passaged every 3 to 5 days. DNA from HBV-infected human hepatoma cell line HLCZ01 was isolated every three days. One microgram of DNA from HBV-infected HLCZ01 cells is used as template for processing quantitative PCR and HBV DNA level in the human hepatoma cell line HLCZ01 is detected. As shown in FIG. 5, such that HBV DNA can be detected in HBV-infected HLCZ01 cells.

According to the preferred embodiment of the present invention, after the human hepatoma cell line HLCZ01 is infected by HBV, HBV level can be detected by quantitative PCR, such that HLCZ01 is further confirmed to have the ability to be infected by HBV. Moreover, HLCZ01 cells can be infected by various genotype of HBV produced both in cell culture and clinically. Based the above mentioned knowledge, the human hepatoma cell line HLCZ01 of the present invention is able to be a cell culture model supporting HBV, and the human hepatoma cell line HLCZ01 of the present invention not only can be used to build animal models for supporting HBV, but also can be used for the preparation, screening or evaluating anti-HBV drugs.

Referring to FIG. 5 of the drawings, the human hepatoma cell line HLCZ01 of the present invention is able to be a cell model supporting hepatitis virus (above described HBV), wherein the amount of HBV DNA in the human hepatoma cell line HLCZ01 is changed with respect to time (days) after the human hepatoma cell line HLCZ01 is infected by HBV.

Figure 9:
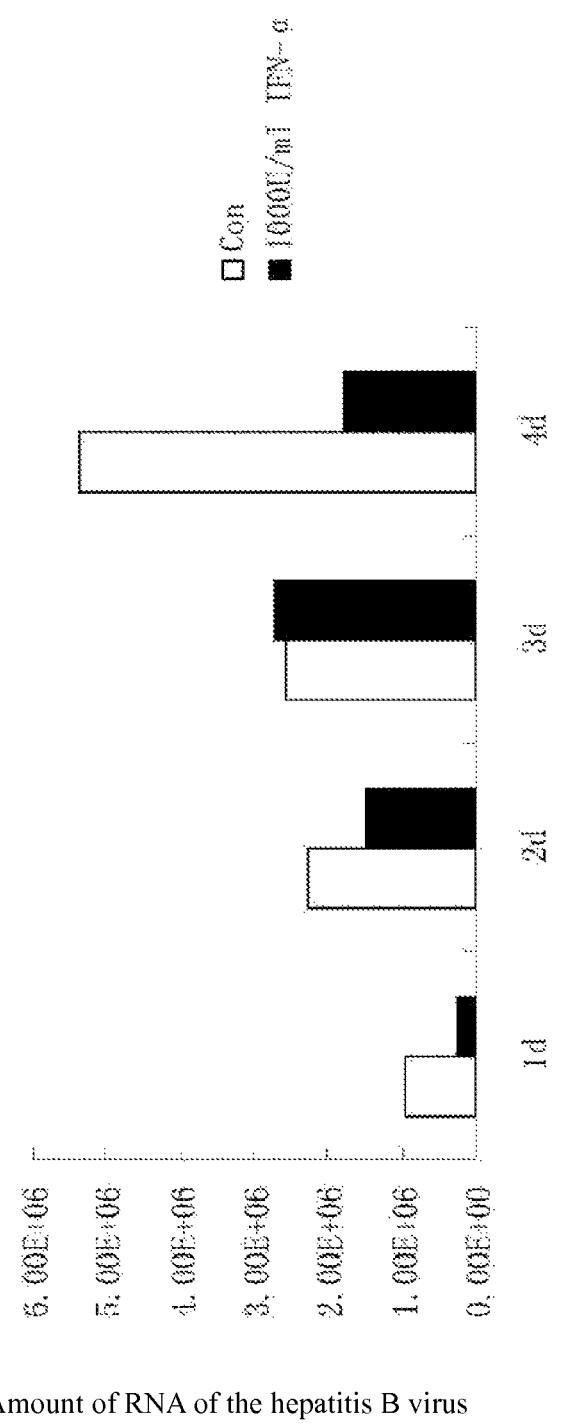
FIG. 9 is a column diagram for the human hepatoma cell line HLCZ01 according to the above second embodiment of the present invention, illustrating the amount of HBV with respect to the amount of interferon used and time (days).

According to the human hepatoma cell line HLCZ01 of the present invention, the human hepatoma cell line HLCZ01 can also be used for the preparation, screening or evaluating the anti-HBV drugs. According to some experiments, after the human hepatoma cell line has been infected by hepatitis B virus, α-interferon which has been used to cure the hepatitis B is able to reduce the amount of HBV in the human hepatoma cell line HLCZ01, as shown in FIG. 9. FIG. 9 shows that the amount of HBV in the human hepatoma cell line HLCZ01 is changed based on the amount of the α-interferon added therein and the processing time (days). Therefore, the human hepatoma cell line HLCZ01 of the present invention can be used for the preparation, screening or evaluating the anti-HBV drugs.

Figure 6:
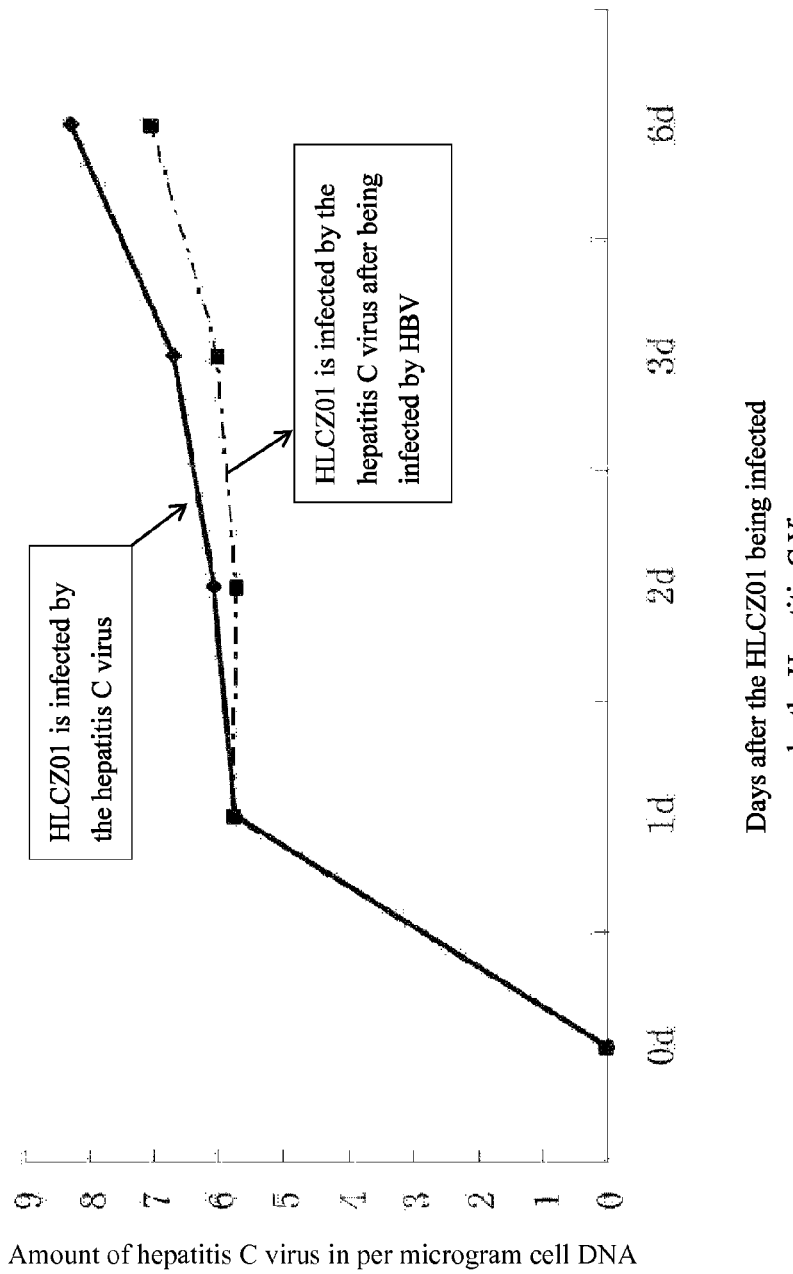
FIG. 6 shows variation curve for two kinds of human hepatoma cell line HLCZ01 (HCV-infected HLC01 cells, and HBV-preinfected HLCZ01 cells, followed with HCV infection) according to the third embodiment of the present invention.

Application Embodiment 3: HLCZ01 is Coinfected with Hepatitis B Virus and Hepatitis C Virus 1. The human hepatoma cell line HLCZ01 which has been infected by the HBV for 53 days is placed on the 6-well cell culture plate (200,000/well). After 24 hours, the medium is replaced to medium containing 2% FBS, and the HCV is used to infect the HBV-infected HLCZ01 cells. After 24 hours, the medium is changed to fresh medium and human hepatoma cell line HLCZ01 is cultured for 1 day, 2 days, 3 days and 6 days respectively. TRIZOL is used to extract total RNA from the above mentioned cells. One microgram of the total RNA is reversely transcribed into cDNA. One microliter of cDNA is used as a template for processing quantitative PCR and HCV RNA in HLCZ01 cells can be detected, as shown in FIG. 6. As shown in FIG. 6, the amount of HCV in human hepatoma cell line HLCZ01 infected by HCV and HBV-preinfected HLCZ01 cells infected by HCV are both increased with respect to the infection time (days).

Figure 7:
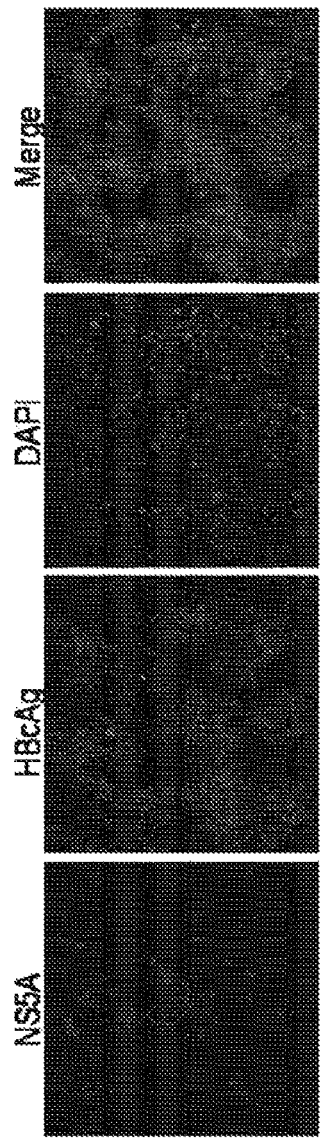
FIG. 7 is a test result for the human hepatoma cell line HLCZ01 being processed by an immunofluorescence process according to the above third embodiment of the present invention.

2. The human hepatoma cell line HLCZ01 which have been infected by the HBV are infected by the HCV for 6 days based on the above mentioned infection method, and the ice-acetone is used to fix viral-infected HLCZ01 cells. The antibodies against HBV core protein antigen and HCV NS5A protein are used to determine the existing of the HBV and HCV, and the results are shown in FIG. 7. As shown in FIG. 7, HBV core antigen and HCV NS5A protein can be detected in the human hepatoma cell line HLCZ01. Moreover, both viral proteins, HBV core antigen and HCV NS5A protein, can be detected within the same HLCZ01 cell, wherein a NS5A diagram of FIG. 7 shows that HCV NS5A protein can be detected in the HLCZ01 cell line, and a HBcAg diagram demonstrates that HBV core antigen can be detected in the HLCZ01 cell line, and a DAPI diagram of FIG. 7 shows cell nuclei which have been stained with DAPI, and a merge diagram is combined the NS5A, HBcAg, DAPI, and Merge diagram of FIG. 7.

According to the preferred embodiment of the present invention, after the human hepatoma cell line is infected by HCV and HBV, the levels of HCV RNA and HBV DNA are detected by quantitative PCR, and such that the HLCZ01 is further confirmed to have the ability to be coinfected by HCV and HBV. Based the above mentioned knowledge, the human hepatoma cell line HLCZ01 of the present invention is able to be a cell model supporting HCV and HBV coinfection. Therefore, the human hepatoma cell line HLCZ01 of the present invention can be used not only for animal models for supporting HCV and HBV coinfection, but also for the preparation, screening or evaluating the anti-HCV and anti-HBV drugs. (Referring to FIG. 6 to FIG. 10)

Figure 11:
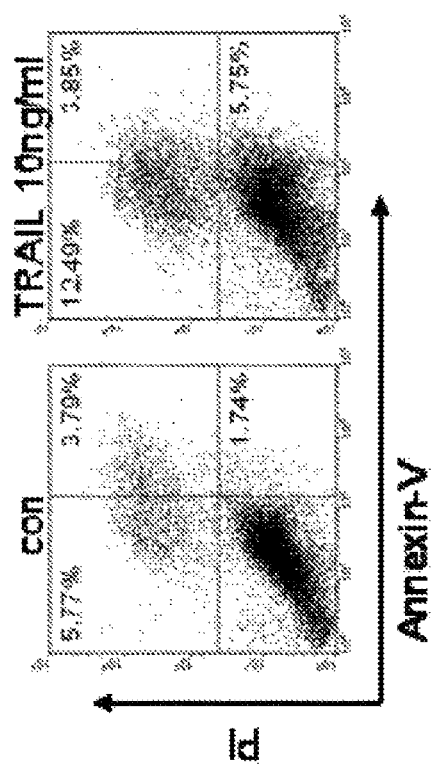
FIG. 11 is a flow cytometry result that demonstrates TRAIL sensitivity for the human hepatoma cell line HLCZ01 treated with TRAIL according to the fourth embodiment of the present invention.

Application Embodiment 4: The Role of HLCZ01 Cell Line in the Preparation, Screening or Evaluating Anti-Tumor Drugs FIG. 11 demonstrates the experimental data which show that TRAIL at the current phase II of clinical trail is able to induce the death of the HLCZ01 cells, so the human hepatoma cell line HLCZ01 of the present invention can also be used for the preparation, screening or evaluating anti-tumor drugs.

Based on the above test results of the present invention, the powerful evidences are proved that HLCZ01 cell line of the present invention is a human hepatoma cell line and the human hepatoma cell line HLCZ01 can be infected by HBV and/or HCV produced both in cell culture and clinically and coinfected with HBV and HCV. The establishment of the human hepatoma cell line HLCZ01 of the present invention can provide a powerful tool for the study of hepatitis viruses, such as HBV and HCV, liver oncology and other researches. HLCZ01 cell line provides a broad application value and application prospect.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hepatoma cell line, wherein said cell line is named as a HLCZ01 cell line which is deposited in the China Center for Type Culture Collection (CCTCC) with Accession No. is CCTCC NO: C201309.

2. The hepatoma cell line, as recited in claim 1, wherein said HLCZ01 cell line is a human hepatoma cell line HLCZ01 having 54 to 63 chromosomes, wherein said human hepatoma cell line HLCZ01 shows a phenomenon of heteromorphic chromosomes after karyotype analysis of chromosome G band, and a marker chromosome appears in a karyotype.

3. The hepatoma cell line, as recited in claim 2, wherein said human hepatoma cell line HLCZ01 is infectable by hepatitis C virus (HCV) and hepatitis B virus (HBV).

4. The hepatoma cell line, as recited in claim 2, wherein said human hepatoma cell line HLCZ01 comprises hepatocyte specific genes ALB and AAT.

5. The hepatoma cell line, as recited in claim 4, wherein said hepatocyte specific genes ALB and AAT are detected by RT-PCR.

6. The hepatoma cell line, as recited in claim 4, wherein said hepatocyte specific genes ALB and AAT are detected by a Western Blot.

7. A cell model for preparation, screening and evaluation of anti-HCV hepatitis virus drugs, which comprises a human hepatoma cell line HLCZ01 having 54 to 63 chromosomes, wherein said human hepatoma cell line HLCZ01 shows a phenomenon of heteromorphic chromosomes after karyotype analysis of chromosome G band, and a marker chromosome appears in a karyotype.

8. The cell model, as recited in claim 7, wherein said human hepatoma cell line HLCZ01 is infectable by hepatitis C virus (HCV) and hepatitis B virus (HBV).

9. The cell model, as recited in claim 7, wherein said human hepatoma cell line HLCZ01 comprises hepatocyte specific genes ALB and AAT.

10. The cell model, as recited in claim 9, wherein said hepatocyte specific genes ALB and AAT are detected by RT-PCR.

11. The cell model, as recited in claim 9, wherein said hepatocyte specific genes ALB and AAT are detected by a Western Blot.

* * * * *